United States Patent [19]
O'Lenick, Jr.

[11] Patent Number: 5,153,294
[45] Date of Patent: Oct. 6, 1992

[54] SILICONE ESTER QUATERNARY COMPOUNDS

[75] Inventor: Anthony J. O'Lenick, Jr., Lilburn, Ga.

[73] Assignee: Siltech Inc., Norcross, Ga.

[21] Appl. No.: 813,449

[22] Filed: Dec. 26, 1991

Related U.S. Application Data

[63] Continuation-in-part of Ser. No. 674,410, Mar. 25, 1991, Pat. No. 5,098,979.

[51] Int. Cl.$^5$ ............................................. C08G 77/04
[52] U.S. Cl. ...................................... 528/26; 528/28; 528/31; 528/15; 548/951; 427/387; 424/70
[58] Field of Search ................ 528/15, 31, 28, 26; 548/951; 427/387; 424/70

[56] References Cited

U.S. PATENT DOCUMENTS

| | | | |
|---|---|---|---|
| 4,185,087 | 1/1980 | Morlino | 424/70 |
| 4,800,077 | 1/1989 | O'Lenick, Jr. et al. | 424/70 |
| 5,073,619 | 12/1991 | O'Lenick, Jr. | 528/26 |
| 5,098,979 | 3/1992 | O'Lenick, Jr. | 528/15 |

*Primary Examiner*—Melvyn I. Marquis
*Assistant Examiner*—Margaret W. Glass

[57] ABSTRACT

The present invention relates to a series of novel ester containing quaternary silicone polymers, useful in softening hair, and fiber and conditioning skin. The compounds of the present invention are prepared by the esterification reaction of chloroacetic acid with a pendant hydroxyl group which is present on a silicone polymer. In a preferred embodiment the hydroxy containing silicone polymer has been alkoxylated with ethylene oxide, propylene oxide or mixtures thereof.

16 Claims, No Drawings

SILICONE ESTER QUATERNARY COMPOUNDS

RELATED APPLICATION

This application is a continuation in part application of U.S. Ser. No. 674,410 filed Feb. 24, 1991, now U.S. Pat. No. 5,098,979.

BACKGROUND OF THE INVENTION:

(1) Field of Invention

The present invention relates to a series of novel silicone ester quaternary silicone polymers useful in softening hair, and fiber and conditioning skin.

Since the compounds of the present invention are high molecular weight silicone polymers, they have a high degree of oxidative stability, even at elevated temperatures. In addition, these compounds are non volatile and unlike many other traditional fatty quaternary compounds are non yellowing when applied to textile substrates and are non irritating to eyes and skin.

The compounds of the present invention are prepared by the reaction of monochloroacetic acid with a pendant hydroxyl group which is present on a silicone polymer, This results in chloro ester which in a subsequent step is reacted with an amine. In a preferred embodiment the hydroxy containing silicone polymer has been alkoxylated with ethylene oxide, propylene oxide or mixtures thereof. The ability to regulate both the type of alkylene oxide and amount of alkylene oxide present in the silicone polymer results in a series of products ranging in water / oil solubility. The technology used to produce the compounds of the present invention is very flexible and allows us to prepare performance tailored molecules for specific applications.

(2) Object of the Invention

It is the object of the present invention to provide a series of novel ester containing quaternary silicone polymers, which are substantive to skin and hair. This substantivity results in superior softening, conditioning and antistatic properties. The presence of the ester functionality results in improved foam properties over the compounds disclosed in the parent application in which this is a continuation in part. The compounds of the present invention contain a fatty portion which is derived from a fatty amine. Incorporation of this type of group into the silicone molecule results in increased solubility in many organic solvents. This ability to marry fatty chemistry with silicone chemistry results in unexpected solubilities and surface active properties. The compounds also contain varying amounts of ethylene oxide and propylene oxide in the molecule. This results in the ability to vary water solubility and introduce an inverse cloud point into the molecule. Inverse cloud point is well known to those skilled in the surfactant art. It is generally found in nonionic surface active agents. It is not found in quaternary compounds. The inverse cloud point is that temperature at which a soluble compound looses it's solubility in water. Inverse cloud point, also called high cloud point, is thought to be associated with the ability of the alkylene oxide chain to hydrogen bond with the water.

It is another objective of the current invention to provide ester containing quaternary silicone polymers which have very low irritation values when applied to skin and eyes. Irritation is a major problem with traditional fatty cationic materials.

Still another object of the present invention is to provide a series of ester containing quaternary silicone polymers which have differing solubilities in water and organic solvents. This is achieved by selection of the hydroxy silicone polymer used as a raw material.

Application of the compounds of the invention can be from solvent, aqueous dispersion or solution, or applied neat in these process. It is anticipated that the effective conditioning concentration of the compound of this invention ranges from 0.1% to 25% by weight.

The silicone polymers, suitable as raw materials, in a preferred embodiment, contain varying amounts of ethylene oxide, propylene oxide or mixtures thereof. The presence of the oxide in the silicone polymer results in compounds with an inverse cloud point. Inverse cloud point phenomenon are well known to those skilled in the art of nonionic surface active agents. The inverse cloud point is defined as a temperature above which the polymer has minimal solubility in water. If heat is applied to an aqueous solution of the nonionic at the inverse cloud point the material will become insoluble, and the solution will turn milky. It is at this point that the polymer has minimal water solubility. Since the product is no longer in solution at above this temperature, it is within this temperature range that the product has maximum substantivity to a fiber. The ability to use temperature to deposit a lubricant, antistat onto a fiber offers a great advantage in cost effectiveness of fiber treatment, and results in less product usage.

(3) Description of the Arts and Practices

Silicone oils (dimethylpolysiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This requires high pressure equipment, surface active agents and generally results in a milky emulsion. Emulsions have experienced stability problems both in terms of freeze thaw instability and upon heating. This has resulted in minimal acceptance of them in commercial products.

The low efficiency of silicone oils is due to the fact that the oil is very water insoluble. Emulsions are generally prepared which contain silicone dispersed in micelles. While this method of application is easier for processing, much of the oil stays in the surfactant micelle and never gets deposited on the fiber. That which does deposit on the fiber surface remains there by hydrophobic binding, not ionic bonding. Since the polydimethylsiloxane is not ionically bonded the effect is very transient. The product is removed with one washing.

Fatty quaternary compounds have been known as softeners for many years. They have a much lower molecular weight than the silicone based compounds of the present invention. For this reason, they are much more irritating to skin and eyes than those materials based upon silicone polymers.

Standard fatty quaternary compounds are prepared by quaternization of a tertiary amine with such agents as benzyl chloride or di-methyl sulfate or di-ethyl sulfate or methyl chloride. These materials are relatively inexpensive but offer several key disadvantages. These include yellowing of fabrics, a tendency to build-up upon repeated treatment, and variability in hand (i.e. softness and feel). Standard softeners used are selected from the following classes:

Class #1. Alkyl Imidazoline Quaternary Compounds made from the quaternization of an imidazoline made by reacting diethylenetriamine, and a high molecular weight fatty acid such as stearic acid. The standard quaternizating agents are di-ethyl sulfate, or methyl chloride, or di-methyl sulfate, or methyl chloride or benzyl chloride.

Class #2. Alkyl or dialkyl tertiary amines quaternized with benzyl chloride or di-ethyl sulfate or methyl chloride or di-methyl sulfate.

Class #3. Quaternary compounds of ethoxylated, propoxylated or nonalkoxylated amido amines derived from the reaction of a high molecular weight fatty acid like stearic acid and a polyamine like diethylene triamine. The standard quaternizating agents are di-ethyl sulfate or di-methyl sulfate or methyl chloride or benzyl chloride.

Class #4. Amido amine salts derived from partially acid neutralized amines.

It is known that under certain catalytic conditions, epichlorohydrin reacts with certain alcohols to give an intermediate which can be used to react with tertiary amines to quaternary compounds. U.S. Pat. No. 3,445,440 to Susi (May 1969) and U.S. Pat. No. 3,517,045 to Susi (June 1970) teaches the use of chlorohydroxypropyl ether to alkylate specific tertiary amines which are the reaction product of a primary fatty amine and ethylene or propylene oxide. The compounds are used as antistatic agents in polymeric compositions such as polyolefin. The antistatic properties of these compounds are achieved by the minimization of static charges on the polymer surface. These anti-static materials are incorporated into the polymer melt and are effective by virtue of their insolubility in the molten polymer. The quaternary compounds migrate to the polymer surface and are effective antistatic agents.

U.S. Pat. No. 4,144,122 to Emanuelsson issued Mar. 13, 1979 teaches that tallow alcohol and certain other higher molecular weight non-guerbet alcohols and their alkoxylates can be reacted with epichlorohydrin, then subsequently with tertiary amines to give compounds suitable for paper debonding.

U.S. Pat. No. 4,215,064 to Lindemann et al issued Jul. 29, 1980 teaches that phosphobetaines can be prepared by the reaction of a phosphate or phosphite salt with epichlorohydrin under aqueous conditions. U.S. Pat. No. 4,283,541 to O'Lenick, et al, issued Aug. 11, 1981 teaches the process for the preparation of the phosphobetaines described in Lindemann (4,215,064). None of these patents teach the compounds of the present invention.

U.S. Pat. No. 4,800,077 issued Jan. 1989 to O'Lenick teaches guerbet alcohol quaternary compounds can be prepared by reacting epichlorohydrin with guerbet alcohols then subsequently reacting the intermediate with amines.

None of the above incorporate silicone into the quaternary compound. Consequently, the unique softening and substantivity properties achieved using the compounds of the present invention are not realized with the above technologies.

THE INVENTION

1) Summary of the Invention

The present invention relates to a series of novel ester containing quaternary silicone polymers. These polymers have a pendant quaternary nitrogen functional group present. The polymers by virtue of the pendent group deposit on hair, skin and fiber surfaces forming effective nonvolatile nonirritating, surface modifying finishes. The compounds of the present invention are excellent conditioners, antistats and non-yellowing, softeners.

The compounds of this invention are represented by the following formula;

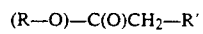

(R—O)—C(O)CH$_2$—R' wherein

R is

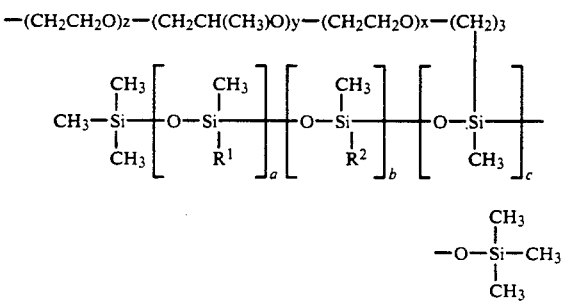

a is an integer from 0 to 200;
b is an integer from 0 to 200;
c is an integer from 1 to 200;
R$^1$ is selected from —(CH$_2$)$_n$CH$_3$ and phenyl;
n is an integer from 0 to 10;
R$^2$ is —(CH$_2$)$_3$—(OCH$_2$CH$_2$)x—(OCH$_2$CH(CH$_3$-))y—(OCH$_2$CH$_2$)z—OH;
x, y and z are integers and are independently selected from 0 to 20;
R' is selected from

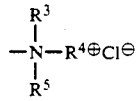

R$^3$, R$^4$, and R$^5$ are each independently alkyl having from 1 to 20 carbon atoms;

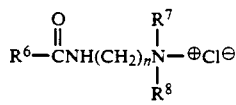

R$^6$ is alkyl having from 6 to 20 carbon atoms,
R$^7$ and R$^8$ are independently methyl or ethyl;
n is an integer from 1 to 5;
and

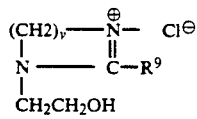

wherein
R$^9$ is alkyl having from 6 to 20 carbon atoms;
v is an integer from 1 to 5.

The products of the present invention are prepared by reaction of a hydroxyl containing silicone polymer with a suitable halo acid, most commonly chloracetic acid.

One method of preparing the reactive hydroxyl containing silicone polymer is to react a silanic hydrogen containing polymer with allyl alcohol or allyl alcohol alkoxylate monomer. Procedures this reaction are well known to those skilled in the art. U.S. Pat. No. 4,083,856 describe suitable processes.

EXAMPLES

Vinyl Intermediate Compounds

Compounds of this class are prepared by alkoxylation of allyl alcohol using methods well known to those skilled in the art. The following are some of the many compounds which can be used to make the products of this invention.

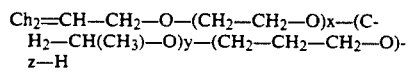

$Ch_2=CH-CH_2-O-(CH_2-CH_2-O)_x-(CH_2-CH(CH_3)-O)_y-(CH_2-CH_2-CH_2-O)_z-H$

| Designation | x | y | z | Molecular Weight |
|---|---|---|---|---|
| A | 3 | 0 | 0 | 189 |
| B | 9 | 27 | 3 | 2,178 |
| C | 11 | 3 | 0 | 718 |
| D | 0 | 0 | 0 | 57 |
| E | 20 | 20 | 20 | 2,940 |
| F | 20 | 0 | 0 | 880 |
| G | 10 | 10 | 10 | 1,470 |

Preparation of Intermediates

Silicone intermediates of the type used to make the compounds of this invention are well known to those skilled in the art. International Publication (*Silicone Alkylene Oxide Copolymers As Foam Control Agents*) WO 86/0541 by Paul Austin (Sep. 25, 1986) p.16 (examples 1 to 6) teaches how to make the following intermediates, and is incorporated herein by reference.

Hydrosilation of Intermediates

Silanic Hydrogen Containing Compounds

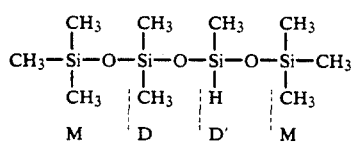

| | | Group Designations | | |
|---|---|---|---|---|
| Example | Austin Example | Group Designation | Average Molecular Weight | Equivalent Molecular Weight |
| 1 | 1 | MD$_{20}$D'$_{3.2}$M | 1,850 | 551 |
| 2 | 4 | MD$_{160}$D'$_5$M | 24,158 | 4,831 |
| 3 | 6 | MD$_{20}$D'$_{10}$M | 2,258 | 225 |

Hydrosilation Compounds

The hydrosilation reaction used to make the compounds of this invention are well known to those skilled in the art. One of many references is International Publication (*Silicone Alkylene Oxide Copolymers As Foam Control Agents*) WO 86/0541 by Paul Austin (Sep. 25, 1986) p. 19.

EXAMPLE 4

To a 22 liter three necked round bottom flask fitted with a mechanical agitator, thermometer with a Thermo-watch temperature regulator, nitrogen sparge tube vented reflux condenser and heating mantle is added 189.0 grams of Vinyl Intermediate Example #A. Next add 225 grams of Silanic Hydrogen Containing Compound Example #3 and 3,000 grams of toluene. Heat to 115 C. to remove azeotropically remove any water and 200 ml of toluene. The temperature is reduced to 85 C. and 3.5 ml of 3% $H_2PtCl_6$ in ethanol is added. Light to then excluded from the flask by covering it with a black cloth. An exotherm is noted to about 95 C., while the contents are stirred for about 2 hours. During this time silanic hydrogen concentration drops to nil. Cool to 65 C. and slowly add 60 g of sodium bicarbonate. allow to mix overnight and filter through a 4 micron pad. Distill off any toluene at 100 C. and 1 torr.

EXAMPLE 5-10

The above procedure is repeated, only this time replacing both the silanic hydrogen compound #3 with the specified number of grams of the specified silanic hydrogen compound and the vinyl intermediate example A with the specified number of grams of the specified vinyl intermediate.

| | Vinyl Intermediate | | Silanic Hydrogen Compound | |
|---|---|---|---|---|
| Example | Example | Grams | Example | Grams |
| 4 | A | 189.0 | 1 | 551.0 |
| 5 | B | 2,178.0 | 2 | 4,831.0 |
| 6 | C | 718.0 | 3 | 225.0 |
| 7 | D | 57.0 | 1 | 551.0 |
| 8 | E | 2,940.0 | 2 | 4,831.0 |
| 9 | F | 880.0 | 3 | 225.0 |
| 10 | G | 1,470.0 | 1 | 551.0 |

Preparation of the Ester Halide

Reaction Sequence

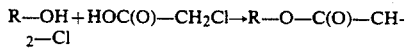

$R-OH + HOC(O)-CH_2Cl \rightarrow R-O-C(O)-CH_2-Cl$

R contains the silicone portion of the molecule.

The following examples further illustrate the objects and advantages of this invention, though it should be understood that the various reactants and amounts thereof, reaction conditions, and other details are merely illustrative and should not be construed to unduly limit this invention.

General Procedure

Place the indicated amount of the dimethicone copolyol produced by the example shown in a suitable vessel. Add the desired amount of catalyst as shown under good agitation and a nitrogen sparge. The specified amount of monochloroacetic acid is added. A molar excess of 0.1 to 0.5 of monochloroacetic acid is added. The temperature is held between 180–225 degrees C. for four to six hours. Reaction progress is monitored by acid value analysis, which is a measure of free chloroacetic acid.

Suitable catalysts are esterification catalysts including, sulfuric acid, p-toluene sulfonic, methane sulfonic, tin metal, zinc metal, titanium metal, organotitinates, organotin compounds, organo zinc compounds, zinc oxide and other esterification catalysts. The preferred catalysts is stannous oxylate.

Chloroacetic acid is Cl—CH$_2$—C(O)—OH. It is also referred to as chloroethanoic acid, monochloroacetic acid, and MCA. It is an item of commerce.

Catalyst "A" below is stannous oxylate, Catalyst "B" is p-toluene sulfonic acid. Both are known esterification catalysts. Catalyst "B" was found to be more aggressive and result in a quicker reaction, however the color of the resulting product was darker. Catalyst "B" gave lighter colors but was somewhat slower. We found that using both the optimum catalyst system was attained.

| Example | Dimethicone Copolyol Example # | Grams | Grams of Chloro-Acetic Acid | Grams of Catalyst "A" | "B" |
|---|---|---|---|---|---|
| 11 | 4 | 740.0 | 100.0 | 0.4 | 0 |
| 12 | 5 | 7009.0 | 100.0 | 2 | 2 |
| 13 | 6 | 943.0 | 100.0 | 0 | 4 |
| 14 | 7 | 608.0 | 100.0 | 4 | 0 |
| 15 | 8 | 7771.0 | 100.0 | 2 | 2 |
| 16 | 9 | 1105.0 | 100.0 | 0 | 4 |
| 17 | 10 | 2021.0 | 100.0 | 4 | 0 |

Quaternary Reaction Sequence

All amine reactants are commercially available from Tomah Products Division of Exxon Chemicals Milton Wi., and various other suppliers.

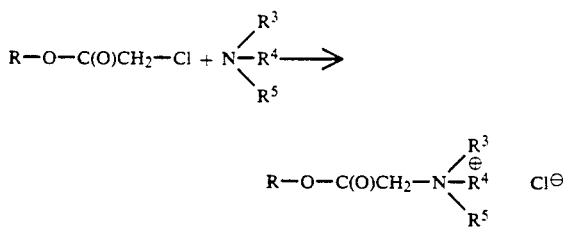

R contains the silicone portion of the molecule.

The following examples further illustrate the objects and advantages of this invention, though it should be understood that the various reactants and amounts thereof, reaction conditions, and other details are merely illustrative and should not be construed to unduly limit this invention.

Amine Reactant Group 1

The reactants are tertiary amines conforming to the following structure;

$$R^4-\underset{\underset{R^5}{|}}{\overset{\overset{R^3}{|}}{N}}$$

| Example Number | R$^3$ | R$^4$ | R$^5$ |
|---|---|---|---|
| 18 | C$_{10}$H$_{21}$ | CH$_3$ | CH$_3$ |
| 19 | C$_{12}$H$_{25}$ | CH$_3$ | CH$_3$ |
| 20 | C$_{14}$H$_{29}$ | CH$_3$ | CH$_3$ |
| 21 | C$_{16}$H$_{33}$ | CH$_3$ | CH$_3$ |
| 22 | C$_{18}$H$_{37}$ | CH$_3$ | CH$_3$ |
| 23 | C$_{20}$H$_{41}$ | CH$_3$ | CH$_3$ |
| 24 | C$_{10}$H$_{21}$ | C$_{16}$H$_{33}$ | CH$_3$ |
| 25 | C$_{12}$H$_{25}$ | C$_{18}$H$_{37}$ | CH$_3$ |
| 26 | C$_{14}$H$_{29}$ | C$_{20}$H$_{41}$ | CH$_3$ |
| 27 | C$_{16}$H$_{33}$ | C$_{10}$H$_{21}$ | CH$_3$ |
| 28 | C$_{18}$H$_{37}$ | C$_{12}$H$_{25}$ | CH$_3$ |
| 29 | C$_{20}$H$_{41}$ | C$_{14}$H$_{29}$ | CH$_3$ |
| 30 | C$_6$H$_{13}$ | C$_6$H$_{13}$ | C$_6$H$_{13}$ |
| 31 | C$_2$H$_5$ | CH$_3$ | C$_2$H$_5$ |
| 32 | C$_{10}$H$_{21}$ | C$_{10}$H$_{21}$ | C$_{10}$H$_{21}$ |

Amine Reactant Group 2

The reactants are amido tertiary amines conforming to the following structure;

$$R^6-C(O)N(H)-(CH_2)_3-\underset{\underset{R^8}{|}}{\overset{\overset{R^7}{|}}{N}}$$

| Example Number | R$^6$ | R$^7$ | R$^8$ |
|---|---|---|---|
| 33 | C$_5$H$_{11}$ | CH$_3$ | CH$_3$ |
| 34 | C$_7$H$_{15}$ | CH$_3$ | CH$_3$ |
| 35 | C$_9$H$_{19}$ | CH$_3$ | CH$_3$ |
| 36 | C$_{11}$H$_{23}$ | CH$_3$ | CH$_3$ |
| 37 | C$_{13}$H$_{27}$ | CH$_3$ | CH$_3$ |
| 38 | C$_{15}$H$_{31}$ | CH$_3$ | CH$_3$ |
| 39 | C$_{17}$H$_{35}$ | CH$_3$ | CH$_3$ |
| 40 | C$_{19}$H$_{39}$ | CH$_3$ | CH$_3$ |
| 41 | C$_{19}$H$_{39}$ | CH$_2$CH$_3$ | CH$_2$CH$_3$ |
| 42 | C$_{11}$H$_{23}$ | CH$_2$CH$_3$ | CH$_2$CH$_3$ |
| 43 | C$_5$H$_{11}$ | CH$_2$CH$_3$ | CH$_2$CH$_3$ |
| 44 | C$_5$H$_{11}$ | CH$_3$ | CH$_3$ |
| 45 | C$_7$H$_{15}$ | CH$_3$ | CH$_3$ |
| 46 | C$_9$H$_{19}$ | CH$_3$ | CH$_3$ |
| 47 | C$_{11}$H$_{23}$ | CH$_3$ | CH$_3$ |
| 48 | C$_{13}$H$_{27}$ | CH$_3$ | CH$_3$ |
| 49 | C$_{15}$H$_{31}$ | CH$_3$ | CH$_3$ |
| 50 | C$_{17}$H$_{35}$ | CH$_3$ | CH$_3$ |
| 51 | C$_{19}$H$_{39}$ | CH$_3$ | CH$_3$ |

Amine Reactant Group 3

The reactants are imidazoline compounds conforming to the following structure;

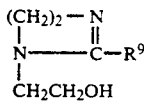

| Example Number | R$^9$ |
|---|---|
| 52 | C$_5$H$_{11}$ |
| 53 | C$_7$H$_{15}$ |
| 54 | C$_9$H$_{19}$ |
| 55 | C$_{11}$H$_{23}$ |
| 56 | C$_{13}$H$_{27}$ |
| 57 | C$_{15}$H$_{31}$ |
| 58 | C$_{17}$H$_{35}$ |
| 59 | C$_{19}$H$_{39}$ |

General Reaction Procedure

The products of the present invention are generally prepared in aqueous solution or dispersion. The preferred concentration is about 50% solids. Additionally, alcohols such as methanol, ethanol, isopropanol, glycols such as ethylene glycol, propylene glycol, polypropylene glycol, polyethylenegylcol, hexylene glycol, and cyclomethicone can be added to improve clarity if desired.

To a suitable flask, equipped with a thermometer and agitator is added the specified amount of water. Next add the specified amount of the type of silicone reactant. Heat to 50 C. Next add the specified amount of the specified amine under good agitation. The reaction mass is heated to 85-95 C. and held from between 5 and 15 hours. The reaction progress is monitored by % inorganic chloride, which approaches 98% of theoretical.

|  | Amine Reactants | | Silicone Reactants | | Water |
|---|---|---|---|---|---|
| Example | Example | Grams | Example | Grams | Grams |
| 60 | 18 | 185.0 | 11 | 834.0 | 1,019.0 |
| 61 | 19 | 201.0 | 12 | 7,103.0 | 7,304.0 |
| 62 | 20 | 227.0 | 13 | 1,037.0 | 1,264.0 |
| 63 | 21 | 253.0 | 14 | 702.0 | 955.0 |
| 64 | 22 | 279.0 | 15 | 7,865.0 | 8,144.0 |
| 65 | 23 | 305.0 | 16 | 1,119.0 | 1,424.0 |
| 66 | 24 | 364.0 | 17 | 3,115.0 | 3,479.0 |
| 67 | 25 | 406.0 | 11 | 834.0 | 1,240.0 |
| 68 | 26 | 458.0 | 12 | 7,103.0 | 8,801.0 |
| 69 | 27 | 364.0 | 13 | 1,037.0 | 1,401.0 |
| 70 | 28 | 406.0 | 14 | 702.0 | 1,108.0 |
| 71 | 29 | 458.0 | 15 | 7,865.0 | 8,323.0 |
| 72 | 30 | 251.0 | 16 | 1,119.0 | 1,370.0 |
| 73 | 31 | 70.0 | 17 | 3,155.0 | 3,225.0 |
| 74 | 32 | 437.0 | 11 | 834.0 | 1,271.0 |
| 75 | 33 | 199.0 | 12 | 7,103.0 | 7,302.0 |
| 76 | 34 | 227.0 | 13 | 1,037.0 | 1,264.0 |
| 77 | 35 | 255.0 | 14 | 702.0 | 957.0 |
| 78 | 36 | 283.0 | 15 | 7,865.0 | 8,148.0 |
| 79 | 37 | 311.0 | 16 | 1,119.0 | 1,430.0 |
| 80 | 38 | 339.0 | 17 | 3,155.0 | 3,494.0 |
| 81 | 39 | 367.0 | 11 | 834.0 | 1,201.0 |
| 82 | 40 | 395.0 | 12 | 7,103.0 | 7,498.0 |
| 83 | 41 | 337.0 | 13 | 1,037.0 | 1,374.0 |
| 84 | 42 | 311.0 | 14 | 702.0 | 1,013.0 |
| 85 | 43 | 227.0 | 15 | 7,865.0 | 9,096.0 |
| 86 | 44 | 640.0 | 16 | 1,119.0 | 1,831.0 |
| 87 | 45 | 4,928.0 | 17 | 3,155.0 | 8,083.0 |
| 88 | 46 | 300.0 | 11 | 834.0 | 1,134.0 |
| 89 | 47 | 328.0 | 12 | 7,103.0 | 7,431.0 |
| 90 | 48 | 1,782.0 | 13 | 1,037.0 | 2,819.0 |
| 91 | 49 | 1,370.0 | 14 | 702.0 | 2,072.0 |
| 92 | 50 | 1,103.0 | 15 | 7,865.0 | 8,968.0 |
| 93 | 51 | 1,131.0 | 16 | 1,119.0 | 2,250.0 |
| 94 | 52 | 184.0 | 17 | 3,155.0 | 3,339.0 |
| 95 | 53 | 212.0 | 11 | 834.0 | 1,046.0 |
| 96 | 54 | 240.0 | 12 | 7,103.0 | 7,343.0 |
| 97 | 55 | 268.0 | 13 | 1,037.0 | 1,305.0 |
| 98 | 56 | 296.0 | 14 | 702.0 | 998.0 |
| 99 | 57 | 324.0 | 15 | 7,865.0 | 8,189.0 |
| 100 | 58 | 352.0 | 16 | 1,119.0 | 1,471.0 |
| 101 | 59 | 380.0 | 17 | 3,155.0 | 3,535.0 |

Applications Evaluation

Applications of the Compounds of The Invention

Wet Comb Out Test

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12-14 seconds.

| Rinse Conditioner (Wet Comb Out Test) | |
|---|---|
| Product | Time in Seconds |
| Product Example 64 | 9 |
| Product Example 92 | 10 |
| Stearyldimethylbenzyl ammonium chloride | 12 |

As can be seen, the compounds of the invention give significant conditioning properties to hair, and coupled with their mild nature with regard to skin and eyes, makes it a prime candidate for cosmetic applications.

What is claimed:

1. A silicone polymer which conforms to the following structure;

$$(R-O)-C(O)CH_2-R'$$

wherein;

R is $$-(CH_2CH_2O)_z-(CH_2CH(CH_3)O)_y-(CH_2CH_2O)_x-(CH_2)_3$$

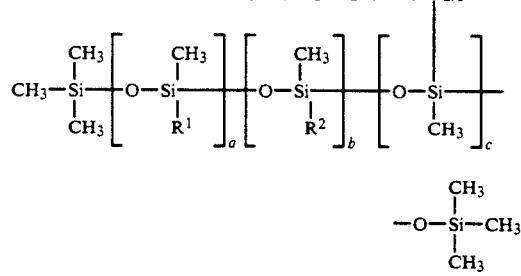

a is an integer from 0 to 200;
b is an integer from 0 to 200;
c is an integer from 1 to 200;
$R^1$ is selected from the group consisting of $-(CH_2)_nCH_3$ and phenyl;
n is an integer from 0 to 10;
$R^2$ is $-(CH_2)_3-(OCH_2CH_2)_x-(OCH_2CH(CH_3))_y-(OCH_2CH_2)_z-OH$;
x, y and z are integers and are independently selected from 0 to 20;
R' is selected from the group consisting of;

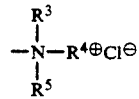

$R^3$, $R^4$, and $R^5$ are each independently alkyl having from 1 to 20 carbon atoms;

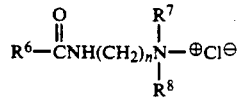

$R^6$ is alkyl having from 6 to 20 carbon atoms;

$R^7$ and $R^8$ are independently selected the group consisting of methyl and ethyl;
and $$(CH_2)_v-\overset{\oplus}{\underset{\underset{CH_2CH_2OH}{|}}{N}}-\overset{}{\underset{C-R^9}{\|}}\quad Cl^\ominus$$

$R^9$ is alkyl having from 6 to 20 carbon atoms;
v is an integer from 1 to 5.

2. A silicone polymer of claim 1 wherein R' is;

$$-\underset{\underset{R^5}{|}}{\overset{\overset{R^3}{|}}{N}}-R^4 \oplus Cl^\ominus$$

$R^3$, $R^4$, and $R^5$ are each independently alkyl having from 1 to 20 carbon atoms.

3. A silicone polymer of claim 1 wherein $R^3$ and $R^4$ are methyl and $R^5$ is alkyl having 18 carbon atoms.

4. A silicone polymer of claim 1 wherein R' is $$R^6-\overset{O}{\overset{\|}{C}}NH(CH_2)_n\underset{\underset{R^8}{|}}{\overset{\overset{R^7}{|}}{N}}-\oplus Cl^\ominus$$

$R^6$ is alkyl having from 6 to 20 carbon atoms;
$R^7$ and $R^8$ are independently selected from the group consisting of methyl and ethyl;
x, y, and z are independently integers each ranging from 0 to 20.

5. A silicone polymer of claim 4 wherein $R^7$ and $R^8$ are methyl and $R^6$ is alkyl having 17 carbon atoms.

6. A silicone polymer of claim 4 wherein $R^7$ and $R^8$ are methyl and $R^6$ is alkyl having 11 carbon atoms.

7. A silicone polymer of claim 1 wherein R' is $$(CH_2)_v-\overset{\oplus}{\underset{\underset{CH_2CH_2OH}{|}}{N}}-\overset{}{\underset{C-R^9}{\|}}\quad Cl^\ominus$$

$R^9$ is alkyl having from 6 to 20 carbon atoms.

8. A silicone polymer of claim 7 wherein $R^9$ is alkyl having 17 carbon atoms.

9. A process for the treatment of fiber which comprises contacting the fiber with an effective conditioning amount of a silicone polymer which conforms to the following structure;

(R—O)—C(O)—CH$_2$—R'

R is
—(CH$_2$CH$_2$O)z—(CH$_2$CH(CH$_3$)O)y—(CH$_2$CH$_2$O)x—(CH$_2$)$_3$ $$-(CH_2CH_2O)z-(CH_2CH(CH_3)O)y-(CH_2CH_2O)x-(CH_2)_3$$

$$CH_3-\underset{\underset{CH_3}{|}}{\overset{\overset{CH_3}{|}}{Si}}-\left[O-\underset{\underset{R^1}{|}}{\overset{\overset{CH_3}{|}}{Si}}\right]_a-\left[O-\underset{\underset{R^2}{|}}{\overset{\overset{CH_3}{|}}{Si}}\right]_b-\left[O-\underset{\underset{CH_3}{|}}{\overset{\overset{CH_3}{|}}{Si}}\right]_c$$

$$-O-\underset{\underset{CH_3}{|}}{\overset{\overset{CH_3}{|}}{Si}}-CH_3$$

a is an integer from 0 to 200;
b is an integer from 0 to 200;
c is an integer from 1 to 200;
$R^1$ is selected from the group consisting of —(CH$_2$)$_n$CH$_3$ and phenyl;
n is an integer from 0 to 10;
$R^2$ is —(CH$_2$)$_3$—(OCH$_2$CH$_2$)x—(OCH$_2$CH(CH$_3$))y—(OCH$_2$CH$_2$)z—OH;
x, y and z are integers and are independently selected from 0 to 20;
R' is selected from the group consisting of;

$$-\underset{\underset{R^5}{|}}{\overset{\overset{R^3}{|}}{N}}-R^4 \oplus Cl^\ominus$$

$R^3$, $R^4$, and $R^5$ are each independently alkyl having from 1 to 20 carbon atoms;

$$R^6-\overset{O}{\overset{\|}{C}}NH(CH_2)_n\underset{\underset{R^8}{|}}{\overset{\overset{R^7}{|}}{N}}-\oplus Cl^\ominus$$

$R^6$ is alkyl having from 6 to 20 carbon atoms;
$R^7$ and $R^8$ are independently selected from the group consisting of methyl and ethyl;
and $$(CH_2)_v-\overset{\oplus}{\underset{\underset{CH_2CH_2OH}{|}}{N}}-\overset{}{\underset{C-R^9}{\|}}\quad Cl^\ominus$$

$R^9$ is alkyl having from 6 to 20 carbon atoms;
v is an integer from 1 to 5.

10. A process of claim 9 wherein R' is;

$$-\underset{\underset{R^5}{|}}{\overset{\overset{R^3}{|}}{N}}-R^4 \oplus Cl^\ominus$$

$R^3$, $R^4$, and $R^5$ are each independently alkyl having from 1 to 20 carbon atoms.

11. A process of claim 9 wherein R' is

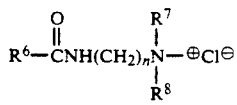

$R^6$ is alkyl having from 6 to 20 carbon atoms;

$R^7$ and $R^8$ are independently selected from the group consisting of methyl and ethyl;

x, y, and z are independently integers each ranging from 0 to 20.

12. A process of claim 11 wherein $R^7$ and $R^8$ are methyl and $R^6$ is alkyl having 17 carbon atoms.

13. A process of claim 11 wherein $R^7$ and $R^8$ are methyl and $R^6$ is alkyl having 11 carbon atoms.

14. A process of claim 9 wherein R' is

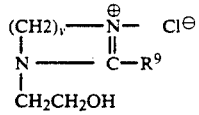

$R^9$ is alkyl having from 6 to 20 carbon atoms.

15. A process of claim 14 wherein $R^9$ is alkyl having 17 carbon atoms.

16. A process of claim 14 wherein $R^9$ is alkyl having 11 carbon atoms.

* * * * *